US006039737A

United States Patent [19]

Dyer

[11] Patent Number: 6,039,737

[45] Date of Patent: Mar. 21, 2000

[54] OPERATION OF A VERTEBRAL AXIAL DECOMPRESSION TABLE

[76] Inventor: Allan E. Dyer, 1400 Dixie Road, Mississauga, Canada, L5M 3B1

[21] Appl. No.: 09/182,250

[22] Filed: Oct. 29, 1998

[30] Foreign Application Priority Data

Aug. 12, 1998 [AU] Australia ............................... 79929/98

[51] Int. Cl.[7] ....................................................... A61B 17/56

[52] U.S. Cl. ................................................. 606/58; 606/54

[58] Field of Search ................................. 606/54, 53, 57, 606/58, 241

[56] References Cited

U.S. PATENT DOCUMENTS 4,995,378 2/1991 Dyer ........................................... 128/75

5,115,802 5/1992 Dyer ........................................... 602/33

*Primary Examiner*—Michael Buiz

*Assistant Examiner*—Jonathan D. Goldberg

*Attorney, Agent, or Firm*—Blackwell Sanders Peper Martin

[57] ABSTRACT

A vertebral axial decompression table is operated by applying a baseline tension to the two table parts, increasing tension to about 50% of maximum above baseline, then logarithmically increasing tension to maximum tension. Thereafter, tension is linearly relaxed back to baseline. This cycle is repeated a programmed number of times to effect a therapy session. Data concerning the table operation is transmitted to allow remote monitoring and re-programming of the table.

23 Claims, 8 Drawing Sheets

| | Ln(t) | TIME | TENSION | |
|---|---|---|---|---|
| Logarithmic Phase Equation<br>$Exp[C^N \times Ln\ 9] = 15.5 + (N \times 8.5)$ | 1.06422 | Slow start to 9 sec. | Slow start to 15.5% plus 8.5 | |
| Slowed start phase | | 1.00 | 1.00 | |
| | | 4.00 | 4.00 | |
| | | 6.00 | 7.00 | |
| | | 7.50 | 11.00 | |
| Logarithmic Phase<br><br>Decompression<br>↓ | 2.1972 | 9.00 | 15.50 | Plus 8.50 |
| | 2.3383 | 10.36 | 24.00 | |
| | 2.4885 | 12.04 | 32.50 | |
| | 2.6483 | 14.13 | 41.00 | |
| | 2.8184 | 16.75 | 49.50 | |
| | 2.9994 | 20.07 | 58.00 | |
| | 3.1920 | 24.34 | 66.50 | |
| | 3.3970 | 29.87 | 75.00 | |
| | 3.6151 | 37.16 | 83.50 | |
| | 3.8473 | 46.87 | 92.00 | |
| | 4.0944 | 60.00 | 100.00 | |
| Retraction Phase<br><br>5 sec delay of retraction phase then add 2.5 sec | | 65.00 | 95.00 | 5 sec delay of phase then deduct 10lb |
| | | 67.50 | 85.00 | |
| | | 70.00 | 75.00 | |
| | | 72.50 | 65.00 | |
| | | 75.00 | 55.00 | |
| | | 77.50 | 45.00 | |
| | | 80.00 | 35.00 | |
| | | 82.50 | 25.00 | |
| | | 85.00 | 15.00 | |
| | | 87.50 | 5.00 | |
| Rest Phase<br>↓ | | 90.00 | 0.00 | |
| | | 95.00 | 0.00 | |
| | | | | |
| | | | | |

TABLE OF TIME vs TENSION IN THE PHASES OF ONE THERAPY CYCLE

FIG. 5

| | Ln(t) | TIME | TENSION | |
|---|---|---|---|---|
| Logarithmic Phase Equation<br>Exp [(N x Ln 1.2089) + Ln9] = 15.5 + (N x 8.5) | Add to Ln(9)<br>0.18972 | Slow start to 9 sec. | Slow start to 15.5% plus 8.5 | |
| Slowed start phase | | 1.00 | 1.00 | |
| | | 4.00 | 4.00 | |
| | | 6.00 | 7.00 | |
| | | 7.50 | 11.00 | |
| Logarithmic Phase | 2.1972 | 9.00 | 15.50 | Plus 8.50 |
| | 2.3869 | 10.36 | 24.00 | |
| | 2.5767 | 12.04 | 32.50 | |
| Decompression | 2.7664 | 14.13 | 41.00 | |
| ↓ | 2.9561 | 16.75 | 49.50 | |
| | 3.1458 | 20.07 | 58.00 | |
| | 3.3355 | 24.34 | 66.50 | |
| | 3.5253 | 29.87 | 75.00 | |
| | 3.7150 | 37.16 | 83.50 | |
| 4.0944 | 3.9047 | 46.87 | 92.00 | |
| | 4.0944 | 60.00 | 100.00 | |
| Retraction Phase | | 65.00 | 95.00 | 5 sec delay of phase then deduct 10lb |
| | | 67.50 | 85.00 | |
| | | 70.00 | 75.00 | |
| | | 72.50 | 65.00 | |
| 5 sec delay of retraction phase then add 2.5 sec | | 75.00 | 55.00 | |
| | | 77.50 | 45.00 | |
| | | 80.00 | 35.00 | |
| | | 82.50 | 25.00 | |
| | | 85.00 | 15.00 | |
| | | 87.50 | 5.00 | |
| Rest Phase | | 90.00 | 0.00 | |
| ↓ | | 95.00 | 0.00 | |
| | | | | |
| | | | | |

TABLE OF TIME vs TENSION IN THE PHASES OF ONE THERAPY CYCLE

FIG. 5a

OPERATION OF A VERTEBRAL AXIAL DECOMPRESSION TABLE

FIELD OF THE INVENTION

This invention relates to a vertebral axial decompression table.

BACKGROUND OF THE INVENTION

Back pain is a common ailment and can represent a painful hindrance that prevents its sufferer from leading a fulfilling life both in leisure and in the workplace. The ailment is very prevalent and there is a need for a non-surgical and efficient form of treatment that would ease this suffering. One form of non-medical treatment is to apply traction to the lumbar region of the spine.

Previous to this invention the commonly used system of applying traction to the lumbar region of a patient was weights and pulleys. The patient was placed supine (face up) on his back and secured to a resting surface. Cords were extended from the patient, looped around suspended pulleys and were tied to raised weights which were released to provide a gravitational tugging. The weights thereby applied traction to the patient's back. This system had only limited success because it did not sufficiently isolate the region of the back, i.e. the lumbar region, to which the traction should have been applied. Further, it would not cause vertebral axial decompression.

SUMMARY OF THE INVENTION

In accordance with the present invention, there is provided a method of operating a vertebral axial decompression table having a first table portion and a second table portion with a controlled means of tensioning the first table portion with respect to the second table portion, comprising the steps of: applying a baseline tension to said table; ncreasing tension applied to said table until said tension is at about 50% of maximum tension above baseline; and increasing tension approximately logarithmically from about 50% of maximum tension above baseline to maximum tension.

BRIEF DESCRIPTION OF THE DRAWINGS

In the figures which disclose example embodiment of the invention,

FIGS. 5 and 5*a* are tables of figures showing the calculation of three phases of a therapy cycle for each of two alternate manners of operation of the table of FIG. 1.

DESCRIPTION OF THE PREFERRED EMBODIMENTS

Figure 1:
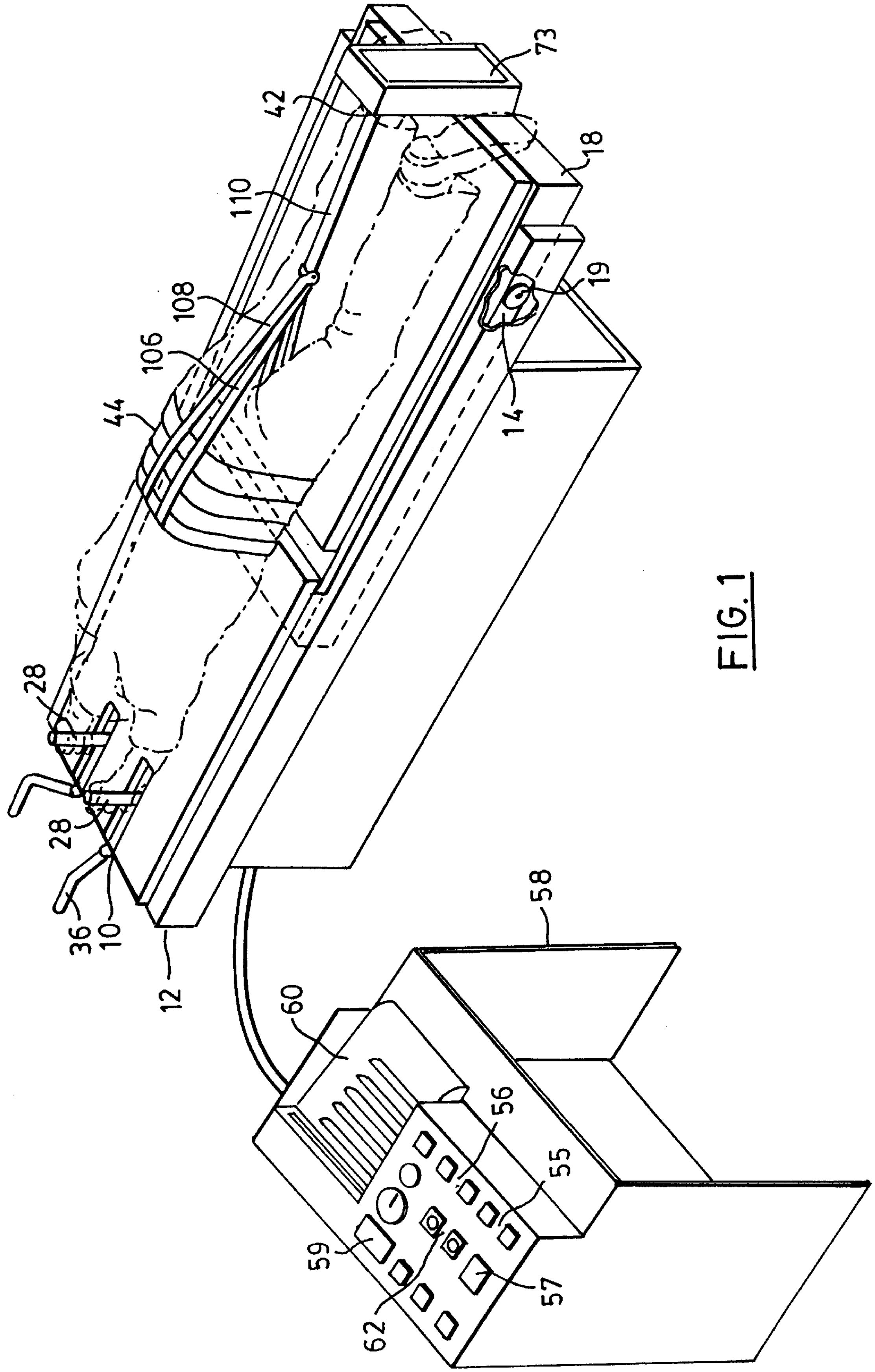
FIG. 1 shows an embodiment of a therapeutic table made according to this invention with a patient drawn in ghost lying prone face down on the table.

The therapeutic table illustrated in the drawings has a table top to support a patient face down as shown in FIG. 1.

The top of the table has an upper body pallet 10 that extends between channel-like side supports 12. The channel-like side supports 12 extend for the full length of the table but the upper body pallet 10 remains stationery to support the upper body of a patient in use. By "upper body", it is meant the area of the body above the waist level. The channel-like side supports 12 extend below the upper body pallet 10 and contain tracks 14 for the rollers 19 of the lower body pallet 18.

Lower body pallet 18 has laterally extending rollers 19 that engage in the tracks 14 and are slidable with respect to the upper body pallet 10. In use, the lower body pallet supports the lower body of the patient. By "lower body" it is meant the portion of the body at and below the waist level.

Figure 4:
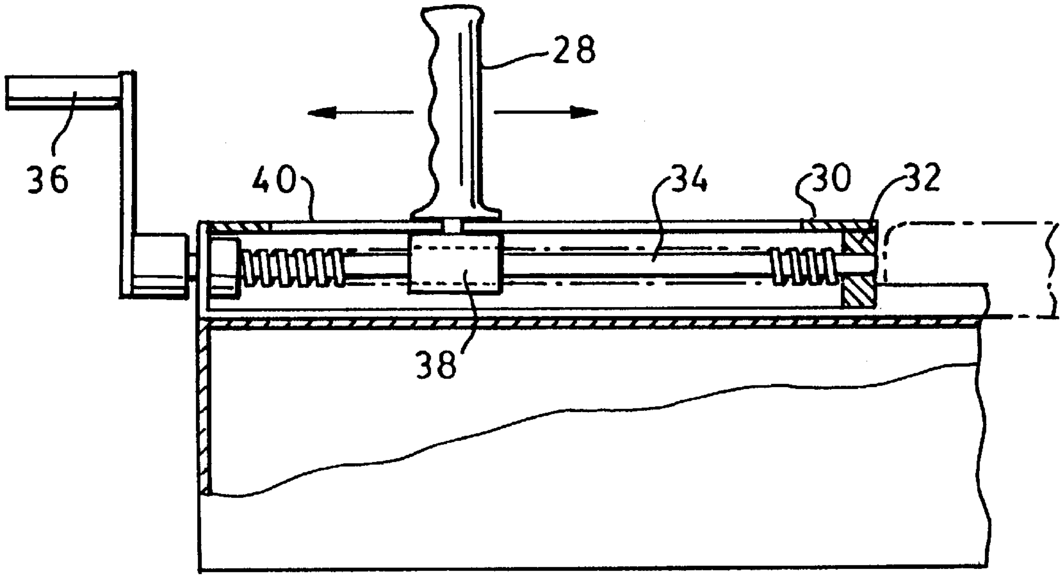
FIG. 4 is a cross-section taken along 4—4 of FIG. 1 showing the adjustable hand grips.

Hand grips 28 are provided. These grips extend from the frame and are adjustable longitudinally of the frame. Their construction is illustrated in FIG. 4. A housing 30 has bearings 32 for the screw 34. Crank 36 is provided to turn the screw in its bearings. A threaded block 38 of the screw extends through a slot 40 in the housing 30 and the handle grip 28 is mounted on the block. It will be apparent that by turning the crank 36, the blocks and their handle grips can be adjusted longitudinally of the table.

Figure 2:
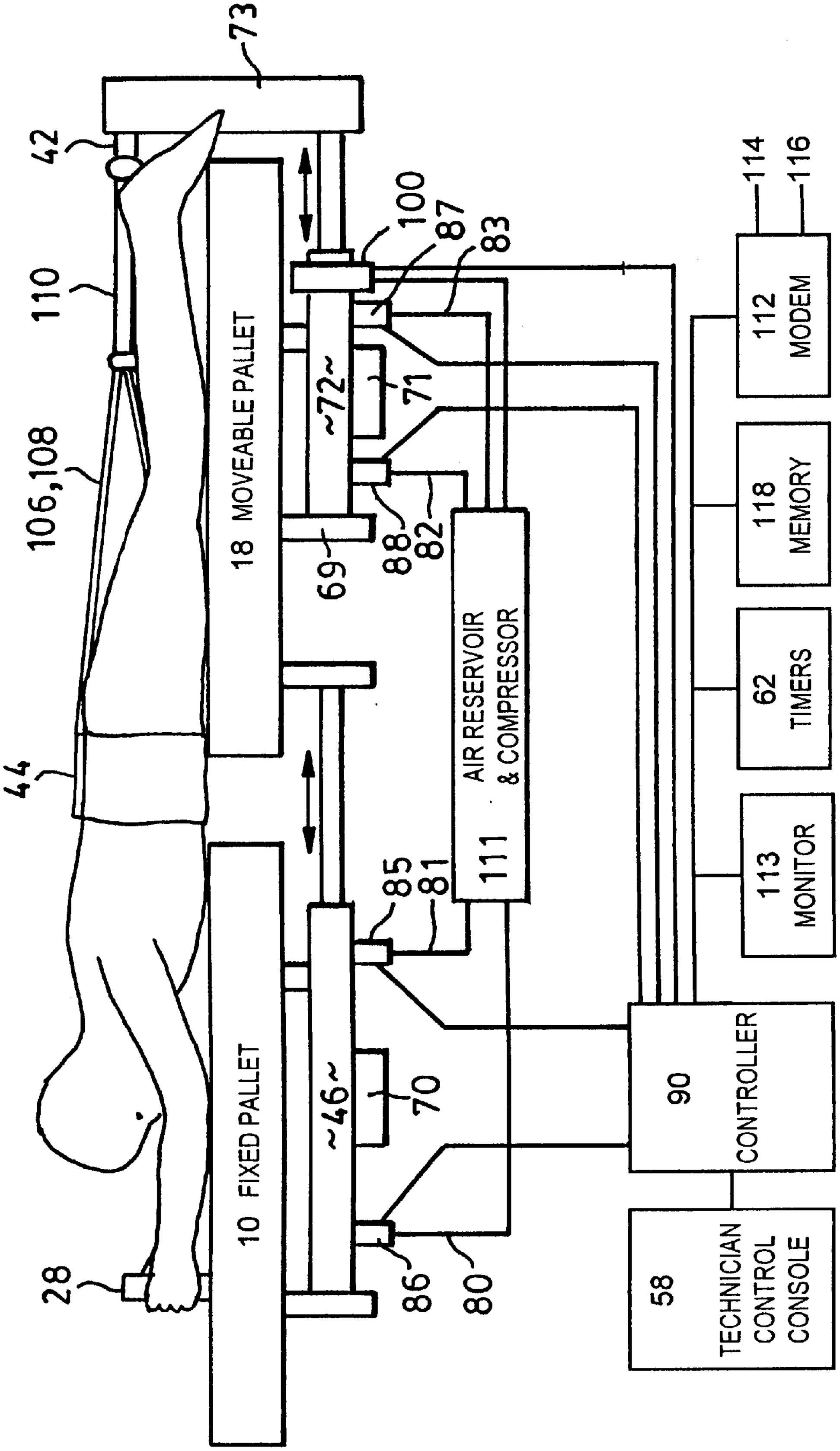
FIG. 2 is a schematic cross-section of the table of FIG. 1.

Referencing FIG. 2 along with FIG. 1, a pre-tensioning cylinder 72 extends between a housing 73 and a fixed support 69 joined to the lower body pallet 18. A therapeutic cylinder 46 extends between the upper body pallet 10 and the lower body pallet 18. The cylinders 46, 72 are fed with pneumatic lines 80, 81 and 82, 83 respectively through solenoid air control valves 85, 86 and 87, 88 respectively. The cylinder assemblies incorporate hydraulic dampers 70 and 71 respectively that control the rate of movement of the table. A controller 90 outputs to a control input of both valves and to lock 100 for the pre-tensioning air cylinder 72.

The housing 73 has a tensionometer 42 that also acts as an anchor for the pelvic belt 44. A clasp is mounted to the centre of the meter 42 to receive an end of a strap 110. In use, the strap is connected to the clasp. This permits an accurate gauging by the meter 42 of the tension being applied to the patient. In alternative arrangements, it is possible to mount a bar, that extends horizontally along an axis perpendicular to the longitudinal axis of the table, to the meter 42. Straps connected laterally to each side of the pelvic belt 44 could then be attached to opposing ends of the bar to permit bilateral traction of the pelvic belt.

The controller receives an input from the tensionometer 42 which constantly measures the amount of tension applied to the pelvic harness fitted to the patient. The controller also receives input from an technician control console 58 on which a therapy technician sets specific parameters that regulate the operation of the equipment as required to customize the therapy for each patient.

When a therapy session is initiated by the technician, the controller 90 receives signals from components that monitor each phase of the therapy session and thereby regulate the automated functions of the equipment. These components include the tensionometer 42, decompression and relaxation timers and cycle counter 57, and limit indicators on the moveable pallet 18. The controller outputs to the solenoid values 85, 86 and 87, 88 that control the air flow and pressure to the pneumatic cylinders and the cylinder locking mechanism 100, a monitor 113 that continually displays and produces a chart recording of the therapy progress, a modem 112 which has a jack 114 for connection to a telecommunications system and a port 116 for connection to an external computer. The controller is connected for two-way communication with memory 118.

Figure 3:
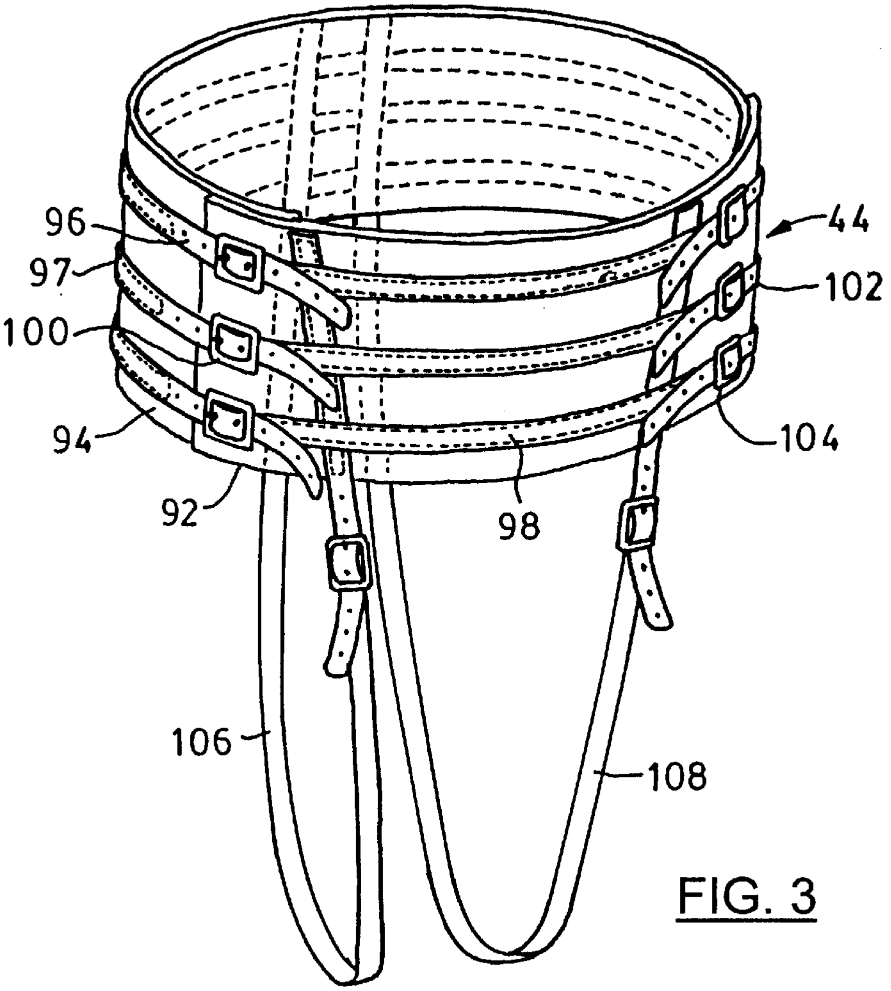
FIG. 3 shows a belt that may be used in combination with the table of FIG. 1.

Referencing FIG. 3, the pelvic belt 44 is secured around the patient's pelvic region. It has two sections 92 and 94 which are secured round the patient's body by straps 96 and 98 and buckles 102 and 104. Extending from the belt are pull straps 106 and 108. As illustrated in FIG. 1, straps 110 connects the straps 106 and 108 to the pelvic belt traction measuring meter 42. In use, when the table separates, the lower-body support pallet 18 slides rearwardly and causes tension to develop to provide traction to the patient's lumbar region. The single strap belt may be replaced with a multi-strap belt if desired.

The pelvic belt is designed so that the straps are connected to the pelvic belt in a manner which locates the posterior straps directly in line with the patient's spinal column. The anterior straps are attached to the belt so as to position the attachment over the anterior superior spine of the Iliac crest of the pelvis.

The lateral traction pelvic belt is designed with straps attached to each part 92 and 94 of the belt.

It will be appreciated that the patient may be further secured at his upper body region to the upper body section by a thoracic vest attached to the upper body section but it has been found that the patient is more comfortable without this attachment. Generally, when the patient's upper body is anchored by voluntary hand gripping, he tends to be more relaxed because he is aware that if the traction applied is excessive he can let go. This means of anchoring the upper body is an important safety feature allowing the patient to end the treatment at any time.

In operation, the pelvic harness 44 is fitted securely around the waist and pelvis of a patient and the patient grasps the handgrips 28, as illustrated in FIGS. 1 and 2. The pelvic harness is connected to the tensionometer 42 by straps 106, 108 and 110 that are attached to and extend from the harness in "diaper fashion" between the legs of the patient being adjustable to accommodate each patient. Via console 58, an operator inputs to the controller 90 the number of cycles for the therapeutic session, the maximum tension to be applied to the patients lumbar spine control, and the length of time, in seconds, for each of the decompression and relaxation phases.

The technician initiates the therapeutic session by activating a pretension ON button 55. Activation of the pretension system causes the controller 90 to signal the solenoid valves 87 and 88 and release the cylinder lock 100 which extends the piston of the pre-tensioning cylinder 72. The rate of travel of the piston of cylinder 72 is controlled by the air flow which is metered on inflow and exhaust. The hydraulic damper 71 is incorporated with the pretension cylinder 72 to assist in ensuring precise movements of the piston.

This increases the tension applied to the patient as the pre-tension cylinder extends the housing 73 on which the tensionometer is mounted. The tensionometer is connected to strap 110 which has been initially adjusted by the technician to remove most of the slack of the pelvic harness. Strap 110 is connected to straps 106 and 108 which extend from and are attached to the pelvic harness. Movement of the cylinder 72 extends the tensionometer housing 73 which draws the pelvic belt in a caudal direction. The weight of the patient resting on the table resists movement and the tension increases on the harness and pelvis of the patient.

The tension applied to the patient is measured by the tensionometer 42 which continually sends the measurements to the controller 90 and the monitor 113. The monitor output is displayed on the LED 59, showing the tension applied in pounds, on the technician's control console 58 and activates a chart recorder 60 which creates a continuous open recorder tracing of the therapy progress which provides a permanent record of the tension, timing and relation between these parameters plus the number of cycles for each therapeutic session.

The controller 90 is designed to linearly increase the tension to a baseline tension which is a pre-selected tension within the range of twenty to twenty-four pounds by applying a separating force and then to maintain this baseline tension throughout the entire therapeutic session.

Once the pre-tension is stabilized at the baseline level, the controller activates the cylinder locking mechanism 100 providing a fixation of the pretension cylinder and housing 73. The controller is programmed to maintain the locked position of the housing 73 relative to the moveable pallet 18 during the decompression and retraction phases.

The operator then activates the system control 56 on the control console 58 which starts the fully automated functions of the equipment and initiates the decompression phase and timer and also activates a three bell signal alerting the patient to grasp the hand grips 28 to fix the upper body against the tension that will be applied when the therapeutic cylinder 46 extends the moveable pallet 18. The tensionometer housing, which is connected to the pelvic harness, is joined to the moveable pallet and locked in place as described above.

When the therapy control 56 is pressed, the controller 90 activates the solenoid pneumatic valves 86 and 85 controlling the air flow into and out of the therapeutic cylinder 46 to extend the cylinder to exert a programmed application of tension described below.

Standard traction tables generally cause reflex muscle guarding and spasm and therefore have proven to be of little or no value in the treatment of discogenic diseases of the lumbar spinal column which prior to the development of non-interventional vertebral axial decompression were treated surgically.

It has been discovered that by using the described table to apply tension logarithmically, reflex muscle guarding and spasm may be avoided. More particularly, the table has been effective in treatment by operating as follows. For an initial phase of treatment, tension is increased slowly from the baseline tension by increasing the separating force on the table. This contributes to patient relaxation thereby allowing accommodation to the tensions applied which is important in achieving success of the treatment. It is preferred that this "slowed start" last for the initial nine seconds and the increase may be linear or a function of the square of the time, increasing tension from baseline to at most 50% of maximum above baseline. This is followed by a logarithmic phase where the tension is increased logarithmically up to a maximum tension, preferably reached at sixty seconds by logarithmically increasing the separating force on the table. The maximum tension may be set any where in the range of 50 lbs. to 100 lbs., with the average setting being 70 lbs.

The slowing rate of increase of the tension implied by the logarithmic function is believed to be the reason that the table avoids reactive muscle problems.

At the end of the decompression phase the tension is linearly released during the retraction phase of the treatment, returning to the baseline tension at a preprogrammed control rate preferably at ninety seconds for the entire decompression plus retraction phases. If tension is released too quickly, or is not maintained at a baseline tension, reactive muscle problems may again result. A linear decrease at a suitable slope to the baseline tension avoids problems. After a rest phase at baseline tension, the process may repeat.

The following function of time versus tension has been found to result in a satisfactory logarithmic phase which has been discovered to reduce the positive pressure normally present in each intervertebral disc to a negative pressure (suction) significantly below zero.

$$\mathrm{Exp}(C^N \times \mathrm{Ln}(BTi)) = BTn + (N \times In)$$

where the left hand side of the equation determines the time, in seconds, and the right hand side of the equation determines the tension as a percent of maximum tension (with 0% tension being the baseline tension) and where:

Exp is the natural exponent, e;

Ln is the natural logarithm;

BTi is the initial time (i.e., time at the beginning of the logarithmic phase);

BTn is the initial tension (i.e., tension above baseline at the beginning of the logarithmic phase as a percent of maximum tension);

In is the % increment chosen for the tension;

N is a positive real number from 0 to $N_{MAX}$; where $N_{MAX}$ is determined by the following equation:

$$In \times N_{MAX} + BTn = 100\%$$

C is a common power factor; where $C = \mathrm{Exp}[(\mathrm{LnLn}Ti_{MAX} - \mathrm{LnLn}BTi)/N_{MAX}]$ and $Ti_{MAX}$ is the time at the end of the logarithmic phase when maximum tension is reached.

For example, choosing BTi to be nine seconds, BTn to be 15%, In to be 8.5% and $Ti_{MAX}$ to be 60 seconds, $N_{MAX}$ is 10 and C is 1.06422. The equation then becomes $$\mathrm{Exp}(1.06422^N \times \mathrm{Ln}(9)) = 15\% + (N \times 8.5)$$

From the logarithmic formula, the following tension/time relationships are apparent: (with 0% tension comprising the baseline tension)

| | |
|---|---|
| At 50% maximum tension | T = 17.10 sec |
| At 60% maximum tension | T = 20.98 sec |
| At 70% maximum tension | T = 26.44 sec |
| At 80% maximum tension | T = 33.91 sec |
| At 90% maximum tension | T = 44.32 sec |

At the beginning of the retraction phase, tension drops 5% of maximum in the first five seconds. Thereafter, the tension drops 10% of maximum tension each 2.5 seconds.

Figure 6:
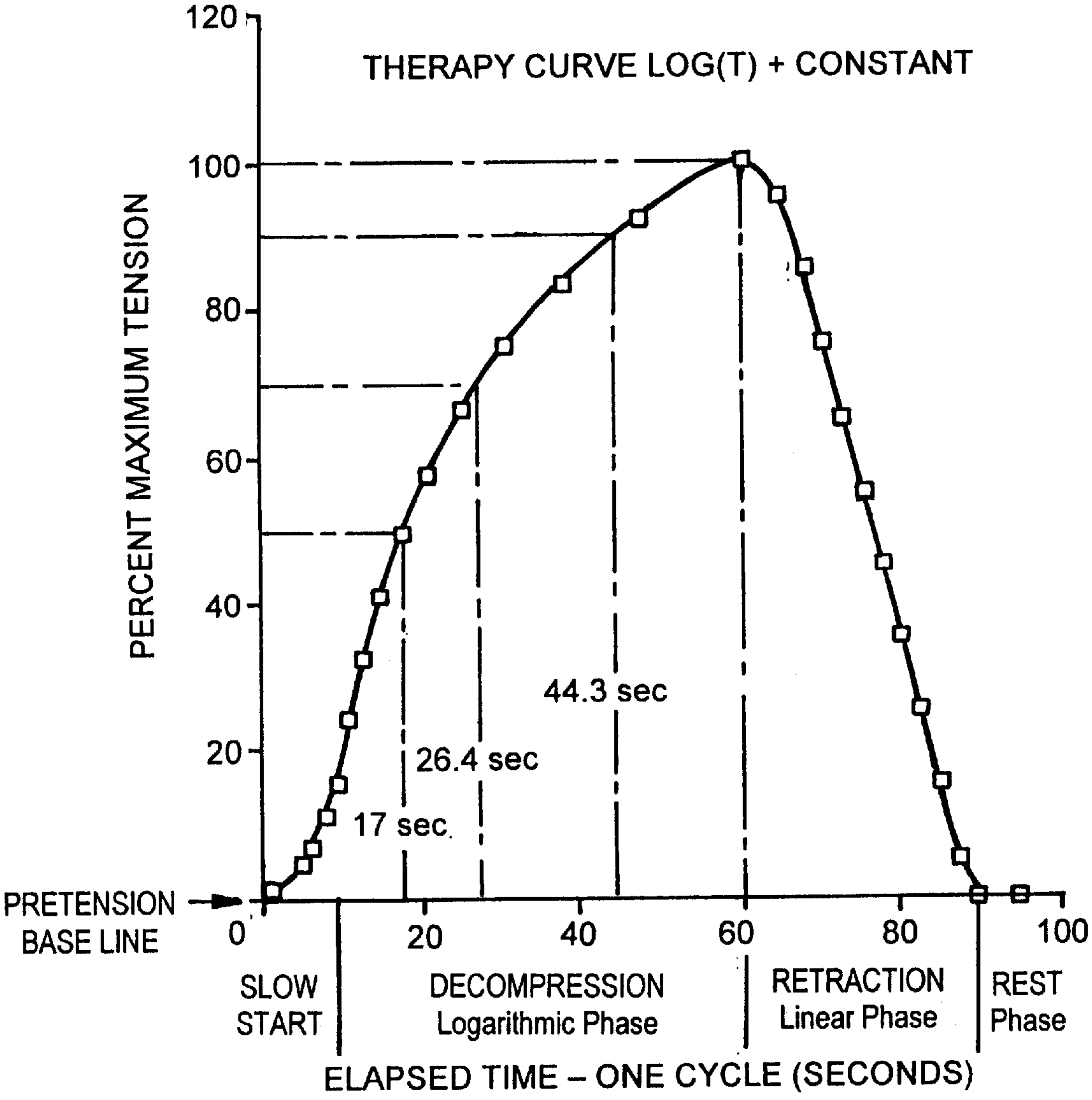
FIGS. 6 and 6*a* are graphs of tension versus time based on FIGS. 5 and 5*a*, respectively, illustrating the operational control of the table and phases of one therapy cycle.

Suitable time versus tension values are tabulated in FIG. 5 and plotted in FIG. 6, with 0% tension comprising the baseline tension.

Another logarithmic curve which has been found to provide satisfactory results in the decompression phase is as follows:

$$\mathrm{Exp}(N \times \mathrm{Ln}K + \mathrm{Ln}(BTi)BTn)) = BTn + (N \times In)$$

where N, BTi, BTn and In are defined as before and where $$K = \mathrm{Exp}[(\mathrm{Ln}Ti_{MAX} - \mathrm{Ln}BTi)/N_{MAX}]$$

Figure 6A:
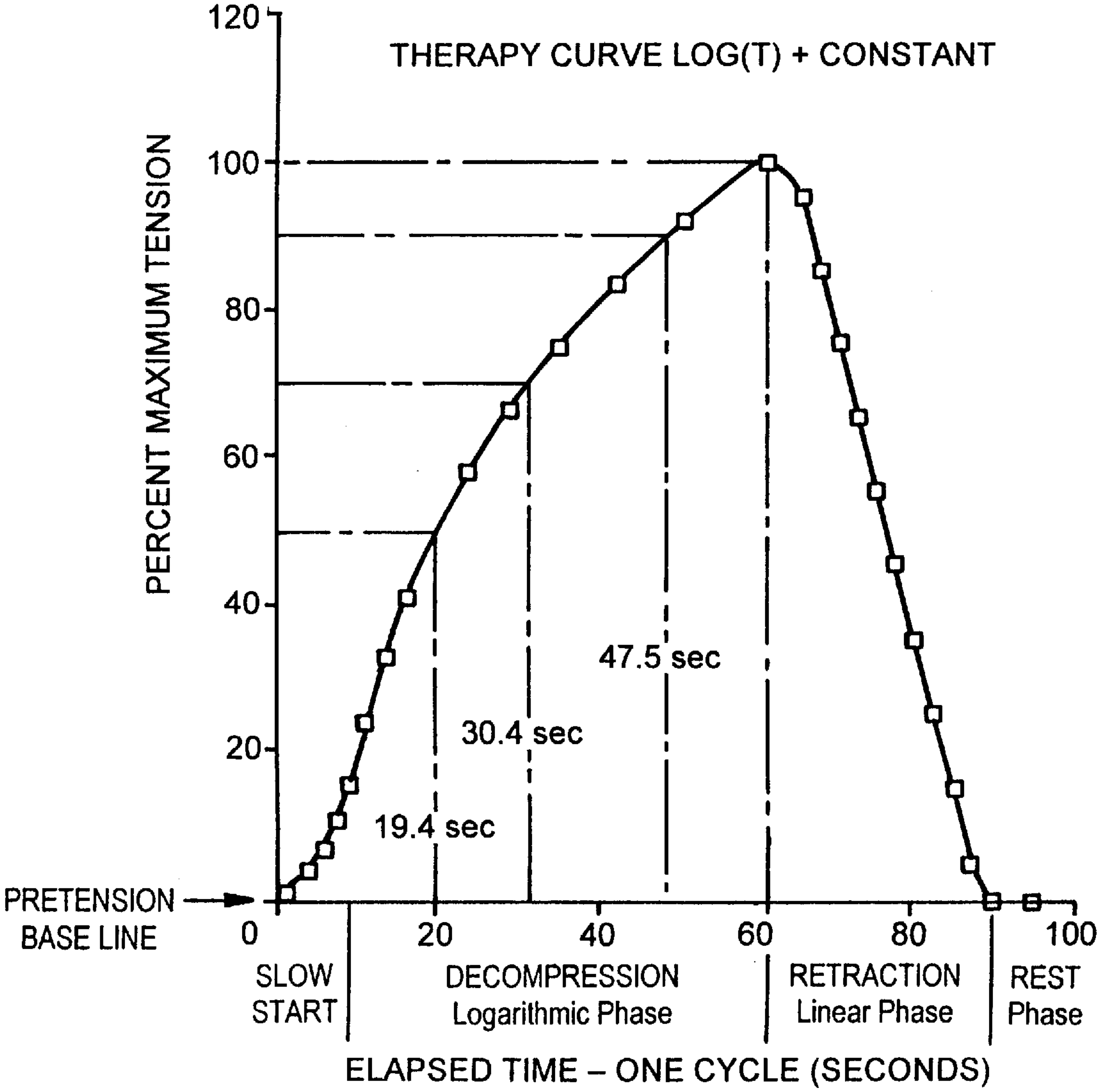

With BTi chosen as nine seconds, BTn as 15%, In as 8.5% and $Ti_{MAX}$ as 60 seconds $N_{MAX}$ is 10 and K is 1.2089 and the time versus tension values resulting are tabulated in FIG. 5*a* and plotted in FIG. 6*a*.

It is apparent from FIGS. 6 and 6*a*, that 50% of maximum tension is reached in the first third of the elapsed time of the decompression phase. Research has shown that the continued increase of the tension to the lumbar spine at a linear rate implied by the time to increase to 50% tension would elicit reflex muscle guarding which can prevent distraction of the lumbar vertebral bodies required to achieve decompression of the intervertebral discs and neural foraminae. However, it has been found that decompression still occurs if the portions of the curve representing increasing tension from 0 to 50% above baseline is linear at a controlled rate of travel approximating that of the logarithmic time/tension relationship to make sure that 50% of the maximum tension is reached within ⅓ of the elapsed time of the decompression phase. The increase in tension above 50% of the maximum must then follow a logarithmic function of time until the maximum tension is reached to avoid reflex muscle reaction.

When tensions sufficient to decompress lumbar structures are repeatedly applied, a progressive controlled rate of distraction of the table during the decompression phase is essential to prevent reactive muscle contractions (guarding) and is therefore vital to the success of the procedure as well as the comfort of the patient.

When the decompression timer 62 completes its part of the cycle, (usually set for 40 to 60 seconds) this signals the controller 90 to activate the solenoid valves 85 and 86 which control the air flow both in and out of the cylinder 46 to end the decompression phase and retract the moveable pallet 18. The rate of travel during the retraction phase is governed by a programmed controlled airflow and exhaust combined with restraint exerted by a hydraulic damper incorporated in the cylinder assembly. The tension applied to the pelvic harness decreases approximately linearly back to the baseline tension of between 20 and 24 lbs. over the next twenty five to thirty seconds.

While it is preferred that the tension decreases from the maximum to the baseline level over twenty-five to thirty seconds, shorter and or longer retraction times may be acceptable within a narrow range. Short retraction times tend to elicit a higher incidence of muscle reaction with certain conditions and longer retraction rates tend to fatigue patients without notable therapeutic gain.

At the end of the retraction phase when the moveable pallet 18 closes on the fixed pallet 10, if the tension applied by the pretension system is sensed by the tensionometer 42 to be above 26 lb. or below 20 lb., the tensionometer signals the controller 90. This releases the cylinder lock 100 and activates the solenoid valves 87 and 88 to appropriately control the air flow and exhaust to adjust the tension applied by the pretension system, up or down as required, to return the baseline level to the resting tension of 20 lb., at which point the controller activates the locking mechanism to hold at that level. This adjustment feature continues to function when necessary to maintain the pretension baseline throughout each of the relaxation phases and is essential to keep the straps from slackening between cycles, as would occur if tension were allowed to drop to zero. The combined system of controller, table position and tensionometer feedback, cylinder adjustment and locking mechanisms are programmed to perform the adjustments gently to ensure that this automated function does not disturb the patient to avoid reflex muscle guarding.

When the table is in the retraction phase, and has reached a tension setting preprogrammed to coincide with closure of the moveable pallet 18 on the fixed pallet 10, the tensionometer 42 signals the controller to start the relaxation phase timer 62 (usually set for forty to sixty seconds). When the moveable pallet is closed on the fixed pallet a "closed" green position light brightens to alert the technician and the controller sounds a single bell chime to notify the patient that they can relax their grasp on the hand grips until the next three bell chime signals the start of another cycle. One therapy cycle is made up of a decompression phase, a retraction phase and a relaxation phase.

During a therapy session if the patient's grasp slips or slack develops in the harness and/or straps allowing the table to travel to its fullest extent of range a red signal light brightens on the control console 58 to notify the technician that adjustments are needed for the table to perform properly. Also if the pretension adjustments during the rest period result in the pretension housing extending to its limit of travel, thus preventing proper baseline adjustments to occur, the controller sounds a repeating tone signal to notify the technician that adjustment in the straps are necessary for the pretension mechanism to maintain the proper baseline between cycles.

From the foregoing, it will be apparent that a therapeutic cycle lasts about ninety seconds in total. There are forty to sixty seconds between cycles. The timing of the cycles and the rest periods is useful in helping the patient accommodate to the strong tensions applied during the decompression phase and are helpful for the reduction of fatigue during the session.

Figure 7:
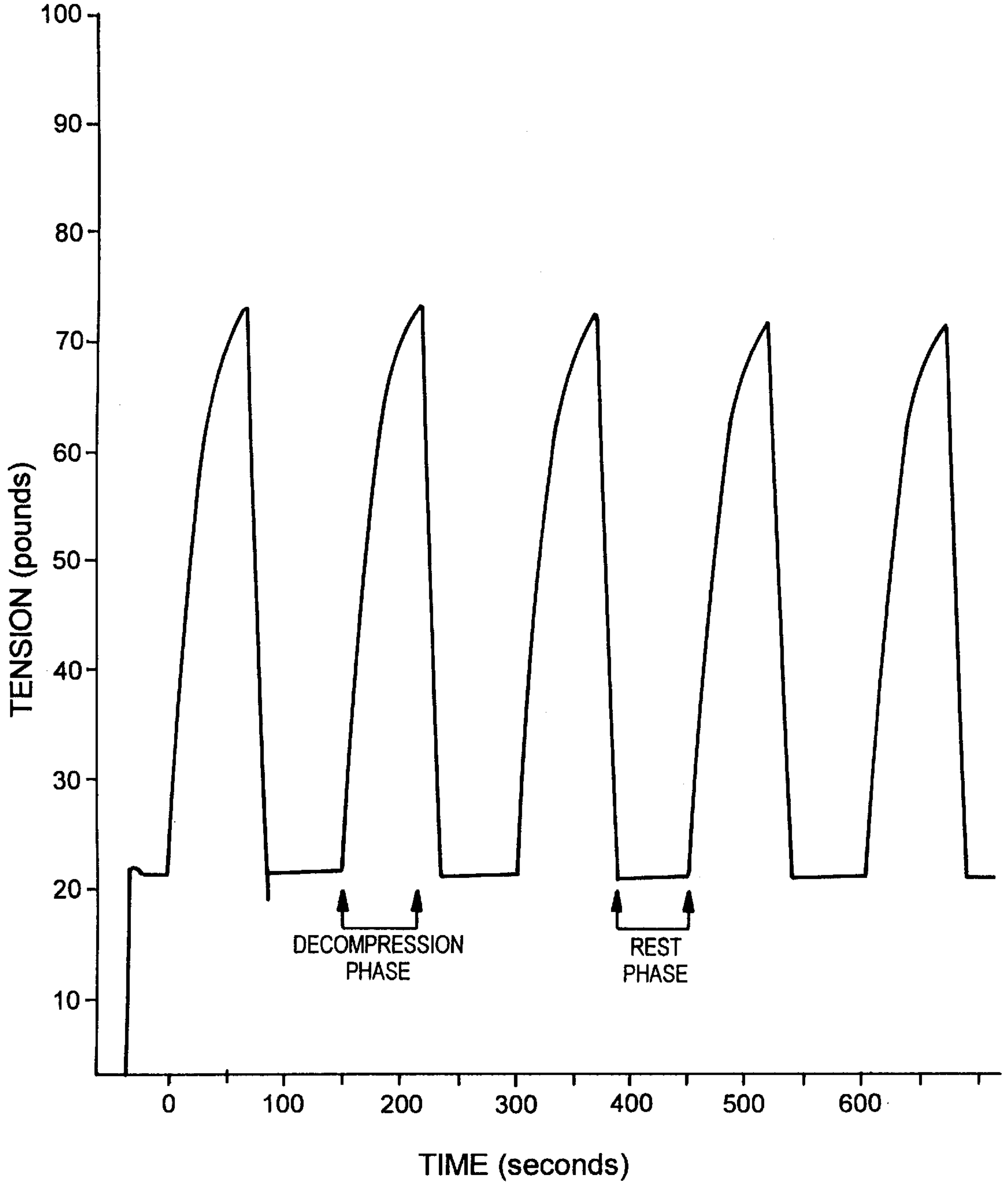
FIG. 7 is a graph showing a series of cycles generated and recorded by the equipment during a therapeutic session.
Figure 6:
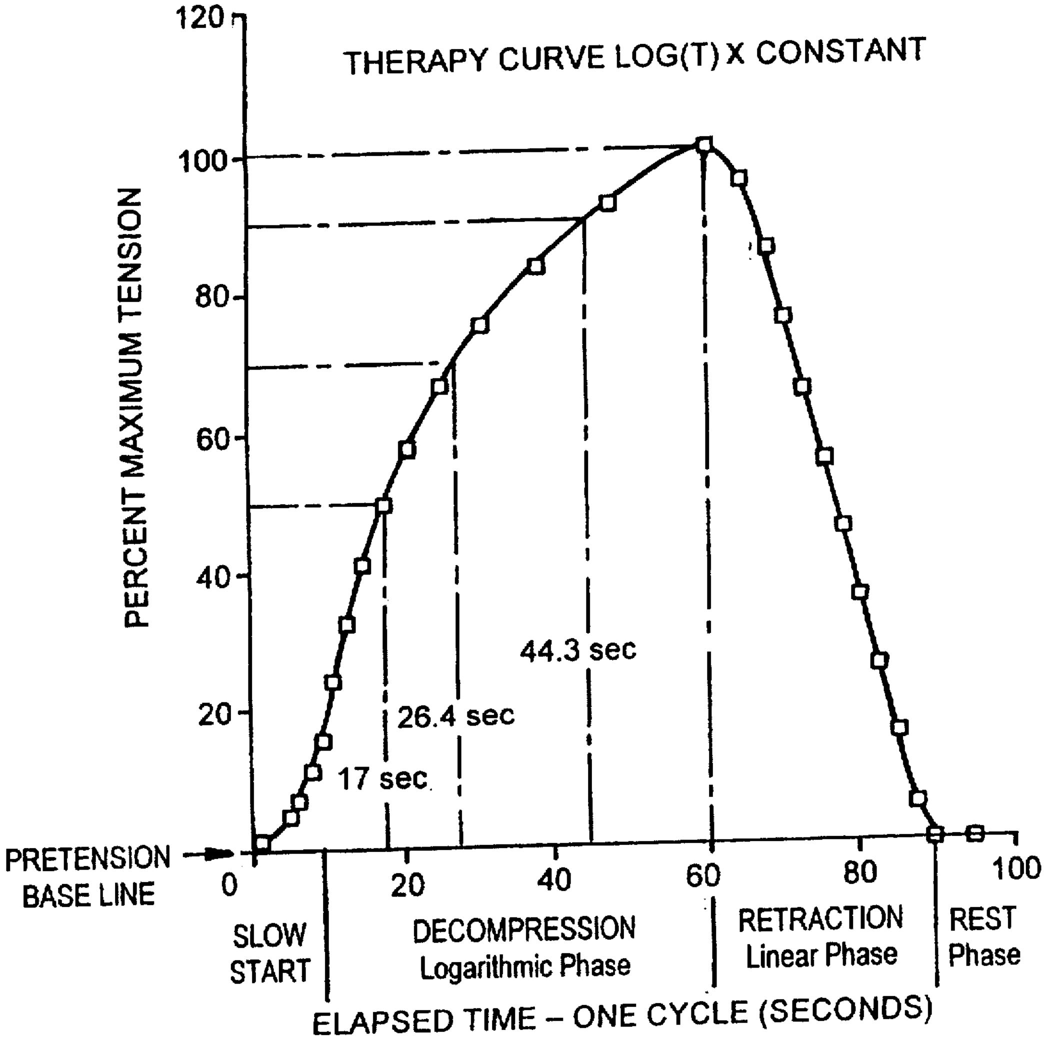

As illustrated in FIG. 7, this cycle from baseline tension to maximum tension and back again is repeated automatically for the selected number of cycles in the therapeutic session, normally fifteen.

At the completion of the therapeutic session when the tension has returned to the baseline after the last cycle, the controller unlocks the pretension cylinder air valve and decreases the pre-tension level to zero, turns the timers off, resets the cycle counter to the preset number, normally fifteen, and returns all functions to the prestart mode in preparation for the next patient's therapy session. The delay in releasing the pretension lock until the table has fully returned is essential to avoid both the therapy and pretension cylinder retracting together which would result in a sudden release of tension and stimulate a muscle guarding reaction. Thereby all tension on the pelvic harness is released allowing the therapist to disconnect the patient's harness from the tensionometer, at which point the patient is assisted off the table and the pelvic harness is removed.

In addition to the passive release of the hand grips which terminates a session, at the discretion of the patient, the controller program incorporates two automated safety features to limit the amount of tension that can be applied. The maximum tension set by the operator cannot exceed 100 lb. This ensures that tension does not exceed the therapeutic range and thereby avoids causing muscle reaction and/or soft tissue stress. If the tension measured by the tensionometer 42 reaches 100 lb. the controller 90 locks the therapy cylinder 46 preventing further increases and holds at that level.

If a patient tugs on the hand grips and raises the tension above the 100 lb. lock to a level of 110 lb. the tensionometer signals the controller which shuts the entire system down and returns the table and pretension to zero. The controller repeatedly blinks the power switch light to signal that this safety features has been activated. Under such conditions the cycles cannot be restarted without turning the main power switch off and back on again.

The retraction rates described are set with standard test equipment which provides a constant resistance on retraction. Tensions tend to fall off more rapidly when treating patients, as tissues relax, especially near the end of the retraction phase. The incorporation of memory and modem components greatly enhances the ability to remotely monitor operating parameters and observe performance and function of the equipment.

The controller may be a microprocessor or a programmable logic controller (PLC). The controller stores information from each therapeutic session. The modem permits a connection with an external computer.

The controller is linked to a modem installed in the control console of the therapeutic table. The control console is equipped with a telephone jack 114 which provides a means of connecting the controller to a remote computer via telephone line linkage. Alternatively the modem can be linked directly to a lap top computer when performing on site service (over port 116).

The computer interlink permits:

1. Retrieval of information pre programmed to be stored in the controller memory, such as the date and time and the following operational events:
   - 1.1 An accumulative number of treatments sessions (each treatment session normally consists of fifteen sequential decompression/relaxation cycles)
   - 1.2 The accumulated total number of decompression/relaxation cycles (this number is a cross check and should be fifteen times the number recorded under 1.1)
   - 1.3 Each month the following counts are retained as cross checks of the way the table is operated or misoperated. This data is deleted at the end of each month.
     - 1.3.1 Number of times the "ON" switch is activated
     - 1.3.2 Number of times the "PAUSE" switch is activated
     - 1.3.3 Number of times the session exceeds the normal count of fifteen cycles
2. Retrieval of the controller operational program permitting remote diagnosis of the operational functions of the equipment.

This function employs a Host Link software for the controller to access a ladder (diagnostic) program which then permits the functions such as the examples below to be monitored.
   - 2.1 Activation of electronic switches on the control panel that turn on or off each function of the unit.
   - 2.2 Activation of the decompression timer signals the controller to operate the solenoid valves to start the decompression phase. The timer governs the length of this phase while the working air pressure set by the therapist governs the strength of the decompression tension applied to the patient's lumbar spine. The controller locks the pretension cylinder solenoid valves during the decompression phase preventing adjustments of this component. This locking function can also be monitored to make sure it is functioning properly during this phase.
   - 2.3 When the decompression timer "times-out" the controller activates solenoid valves allowing the table to retract at a programmed rate to the resting closed position. Fives seconds after the tension decreases to the upper set point of the signal conditioner (26 lb.) the controller releases the lock on the pretension unit and activates the pretension solenoid valves to adjust and hold the programmed tension during the relaxation phase.
   - 2.4 The relaxation timer is activated when the tension reaches the upper set point on the signal conditioner. This governs the length of the relaxation phase of the cycle. The controller responds if tensions below or above the set points occur during the relaxation phase to adjust the pretension unit to maintain the resting tension. The various operating components can be monitored and compared to the ladder program to determine whether the unit is functioning properly and/or diagnose malfunctions.

2.5 The activation of various components on the equipment that signal the presence or absence of functions such as:

2.51 Limit switches that are activated by the moveable upper section of the table in fully open or closed position.

2.52 Limit switches that signal when the oil reservoirs require attention. This prevents failure of the hydraulic cylinders that assist in controlling the precision movements of the pretension unit and moveable section of the table.

3. Deletion of the operational program can be employed to shut down the controller and thereby stop the equipment from functioning if necessary for safety or security reasons. The controller can be preprogrammed to shut down the operation of the equipment under specified conditions for safety and security reasons.

4. The controller can be re-programmed by linkage to a remote computer via the modem if necessary.

5. Standard Therapy Curves

The controller memory is programmed to record the tensions recorded during a typical therapy sequence. This capability provides for the retrieval of data, in real time, produced in the normal operation of the Table for two important system checks.

i) Remote monitoring of an actual treatment session while being conducted on a patient.

ii) Transmission of a standard therapy curve as it is being developed on a Table located in a clinic. Standard curves are routinely generated for standardization of the performance of the Table. The standard curve is generated on all Tables as an important record in the quality control testing of the finished product and this record is filed as part of the Device Master Record for each Table. Creation and maintenance of the Device Master Record is required by the FDA as part of Good Manufacturing Practice (GMP) regulations.

Generation of this quality control measure of performance and retrieval, in real time, from a clinic can then be compared to the master record.

The operational sequence of the various components of the Table may be downloaded from the controller and checked against the following proper operational sequence.

Table at Rest

Power switch

Table closed limit signal

Pretension cylinder air valves (consistent with pretension held closed)

Therapy cylinder air valves (consistent with moveable pallet held closed)

Pretension Phases Initiated

Pretension switch enabled

Pretension cylinder air valves and locking mechanism valve enabled (consistent with extension of pretension mechanism)

Therapy cylinder air valves (consistent with moveable pallet held closed)

Table closed limit signal

Pretension Holding at Proper Tension (20 lb.)

Tensionometer set points (consistent with pretension holding of 20 lb.)

Pretension cylinder air valves and locking mechanism (consistent with fixation at programmed baseline tension)

Therapy cylinder air valves (consistent with moveable pallet held closed)

Table closed limit signal

Decompression Phase

Therapy switch

Decompression timer enabled

Therapy cylinder air valves enabled (consistent with therapy cylinder extending)

Table limit switches (consistent with table distracting. The fully distracted position signal should be OFF in normal operation)

Tensionometer set points (lower and upper activated as tension passes these programmed points)

Retraction Phase

Decompression timer inactivated

Therapy cylinder air valves (consistent with moveable pallet retracting)

Pretension air valves and locking mechanism (consistent with fixed position)

Table position signals (consistent with moveable pallet away from limits)

Relaxation Phase

Relaxation timer - enabled (on when tension reaches upper set point (26lb.))

Tensionometer set points (consistent with baseline tension holding except for intermittent adjustments when pretension air valves and locking mechanism enabled Table limit switch (consistent with closure of table)

Therapy cylinder air valves (consistent with closure and holding moveable pallet)

A method is therefore provided to remotely observe and monitor the operation of a vertebral axial decompression table during a standardized test operation and/or during an actual therapeutic session with a patient. This allows comparison of such functions in real time for both mechanical diagnostic purposes as well as therapeutic usage. For this purpose a standardized therapeutic curve has been developed to which the operation and performance of a table in the field can be compared and assessed. The application of the technology described in this submission provides scientific methods to calibrate equipment at regular intervals and if necessary remotely recalibrate equipment to maintain optimum performance.

A method is also provided to remotely monitor the function and operation of the equipment and to diagnose situations that may be of concern to operators. There is also the ability to upload information and/or reprogram operating procedures where indicated. This will provide great reassurance to operators and help reduce down time to a minimum by facilitating rapid remote diagnostic assessment. The ability to input as well as down load information makes it possible to shut down equipment in the event of malfunction or where the equipment is not being used properly according to the therapeutic protocol.

Optionally, the manually operated controls and switches on the technician's control console may be replaced with operational software and a control CPU and keyboard for uploading functional information and instructions in addition to the current data monitoring and storage capabilities.

In addition the table may be constructed with a single cylinder that is designed to perform both the pretension and therapy functions. This cylinder may be instructed by the controller to first achieve the desired baseline tension and then subsequently, apply the therapeutic tension cycle. Optionally, the cylinder could be replaced with other tensioning mechanisms, such as servo controlled mechanical drive systems.

Other modifications will be apparent to those skilled in the art and, therefore, the invention is defined in the claims.

What is claimed is:

1. A method of decompressing a spinal column of a patient, comprising:

tensioning the spinal column with an initial tension;

approximately logarithmically increasing tension up to a pre-selected tension so as to avoid reflex muscle reaction.

2. The method of claim 1 wherein said step of tensioning with an initial tension comprises increasing tension according to approximately a linear function of time from a baseline tension to said initial tension.

3. The method of claim 1 wherein said tension is increased approximately logarithmically at least from 50% of the pre-selected tension above a baseline tension to the pre-selected tension.

4. The method of claim 3 wherein said baseline tension is between 20 lbs and 24 lbs. and the pre-selected tension is between 50 lbs. and 100 lbs.

5. The method of claim 3 wherein said step of tensioning with an initial tension comprises increasing tension according to approximately a linear function of time from a baseline tension to said initial tension.

6. The method of claim 3 wherein said step of tensioning with an initial tension comprises increasing tension as a function of a square of time from a baseline tension to said initial tension.

7. The method of claim 3 wherein said tension is increased according to approximately a linear function of time to about 50% of the pre-selected tension above the baseline tension.

8. The method of claim 4 wherein said tension is increased from the baseline tension to the pre-selected tension in about sixty seconds.

9. The method of claim 3 wherein said tension is increased logarithmically in accordance with the following function of time versus tension:

$$\mathrm{Exp}(C^{N}\times \mathrm{Ln}(BTi))=BTn+(N\times In)$$

where,

Exp is the natural exponent, e;

Ln is the natural logarithm;

BTi is an initial time (i.e., time at the beginning of the logarithmic phase);

BTn is an initial tension (i.e., tension above baseline at the beginning of the logarithmic phase as a percent of maximum tension);

In is the % increment chosen for the tension;

N is a positive real number from 0 to $N_{MAX}$; where $N_{MAX}$ is determined by the following equation:

$$In\times N_{MAX}+BTn=100\%$$

C is a common power factor; where $C=\mathrm{Exp}[(\mathrm{LnLn}Ti_{MAX}-\mathrm{Ln}(\mathrm{Ln}BTi))/N_{MAX}]$ and $Ti_{MAX}$ is the time at the end of the logarithmic phase when maximum tension is reached.

10. The method of claim 3 wherein said tension is increased logarithmically in accordance with the following function of time versus tension:

$$\mathrm{Exp}(N\times \mathrm{Ln}K+\mathrm{Ln}(BTi))=BTn+(N\times In)$$

where,

Exp is the natural exponent, e;

BTi is an initial time (i.e., time at the beginning of the logarithmic phase);

BTn is an initial tension (i.e., tension above baseline at the beginning of the logarithmic phase as a percent of maximum tension);

In is the % increment for the tension;

Ln is the natural logarithm;

N is a positive real number from 0 to $N_{MAX}$, where $In\times N_{MAX}+BT_{n}=100\%$ K is a constant; where $K=\mathrm{Exp}[(\mathrm{Ln}Ti_{MAX}-\mathrm{Ln}BTi)/N_{MAX}]$.

11. The method of claim 4 further comprising the step of releasing the tension at a controlled rate necessary to ease the tension back to the baseline tension without eliciting reflex muscle reaction.

12. The method of claim 11 wherein the tension is released according to approximately a linear function of time.

13. The method of claim 12 wherein said tension decreases to the baseline tension in about twenty-five to thirty seconds.

14. The method of claim 11 including repeating the steps of tensioning with an initial tension and increasing tension logarithmically after the tension has returned to said baseline tension.

15. A method of decompressing a spinal column of a patient comprising the steps of:

tensioning the spinal column to a baseline tension approximately logarithmically increasing the tension up to a pre-selected tension so as to avoid reflex muscle reaction in a decompression phase;

releasing the tension at a controlled rate necessary to ease the tension to the baseline tension without eliciting reflex muscle reaction in a retraction phase;

maintaining the baseline tension in a relaxation phase; and repeating in cycles decompression, retraction and relaxation phases.

16. The method of claim 15 including the step of linearly increasing tension from baseline tension to an initial tension prior to logarithmically increasing the tension.

17. A method of operating a vertebral axial decompression table having a first table portion and a second table portion comprising:

applying a separating force to said table portions to a baseline level;

increasing said separating force to an initial force of up to 50% of a maximum separating force above the baseline level;

increasing said separating force approximately logarithmically from said initial force to said maximum separating force.

18. The method of claim 17 wherein said step of applying a separating force to an initial force comprises increasing force from said baseline level according to approximately a linear function of time.

19. The method of claim 18 further comprising the step of decreasing said separating force back to the baseline level.

20. The method of claim 19 wherein said separating force is decreased approximately according to a linear function of time.

21. The method of claim 20 wherein said steps of increasing and decreasing said separating force are controlled by an electronic controller.

22. The method of claim 21 wherein said electronic controller is controlled by an external computer linked to said electronic controller.

23. A method of operating a vertebral axial decompression table to yield an automated repetition of cycles, comprising the steps of increasing a separating force from a baseline separating force to an initial force of up to 50% of a maximum separating force above the baseline separating force, increasing said separating force approximately logarithmically from about 50% of said maximum separating force above the baseline separating force to said maximum separating force, decreasing said separating force approximately according to a linear function of time back to the baseline separating force and repeating said steps of increasing and decreasing said separating force.

* * * * *

UNITED STATES PATENT AND TRADEMARK OFFICE
CERTIFICATE OF CORRECTION

PATENT NO. : 6,039,737
DATED : March 21, 2000
INVENTOR(S) : Allan E. Dyer

It is certified that error appears in the above-identified patent and that said Letters Patent is hereby corrected as shown below:

Drawings,
Sheet 6, Figure 6, at the top of the figure, delete "Therapy Curve Log (T) + Constant" and insert -- Therapy Curve Log (T) x Constant --

Column 5,
Line 56, delete the equation "Exp(NxLnK+Ln(BTi)BTn))=BTn+(NxIn)" and insert the following equation -- Exp (N x Ln K + Ln(BTi)) = BTn + (N x In) --

Column 11,
Line 27, delete "lbs" (first occurrence) and insert -- lbs. --

Signed and Sealed this

Nineteenth Day of March, 2002

*Attest:*

JAMES E. ROGAN
*Director of the United States Patent and Trademark Office*

*Attesting Officer*